United States Patent [19]

Pruett et al.

[11] 4,360,475

[45] Nov. 23, 1982

[54] TRANSITION METAL BIMETALLIC CLUSTERS OF RUTHENIUM WITH THALLIUM, INDIUM AND GALLIUM

[75] Inventors: Roy L. Pruett, New Providence; John S. Bradley, Scotch Plains, both of N.J.

[73] Assignee: Exxon Research and Engineering Co., Florham Park, N.J.

[21] Appl. No.: 252,050

[22] Filed: Apr. 8, 1981

[51] Int. Cl.$^3$ .............................................. C07F 9/66
[52] U.S. Cl. ............................... 260/441; 260/429 R; 252/431 R; 252/431 N
[58] Field of Search ........................... 260/429 R, 441

[56] References Cited

U.S. PATENT DOCUMENTS

| | | | |
|---|---|---|---|
| 3,786,132 | 12/1974 | Dawes et al. ........................ | 423/417 |
| 3,793,355 | 11/1974 | Wilkinson ........................... | 260/429 |
| 3,974,259 | 9/1976 | Brown ................................ | 423/249 |
| 3,989,799 | 7/1976 | Brown ................................ | 423/249 |
| 4,115,428 | 8/1978 | Vidal et al. ........................ | 260/449 |
| 4,201,714 | 5/1980 | Hughes .............................. | 260/441 |
| 4,301,086 | 11/1981 | Pruett et al. ..................... | 260/438.1 |

OTHER PUBLICATIONS

John S. Bradley et al., Journal of Organometallic Chemistry, vol. 184, pp. C33–C35, 1980.
Vincenzo G. Albano et al., Journal of the Chemical Society, Dalton, 1980, pp. 52–54.

*Primary Examiner*—Helen M. S. Sneed
*Attorney, Agent, or Firm*—James H. Takemoto

[57] ABSTRACT

Novel bimetallic cluster compounds of the formula $[M]_n[(Ru_6C(CO)_{16})_2L]$ where M is a cation, L is Tl, In or Ga, and n is a number which satisfies valence requirements. These compounds are useful as homogeneous and heterogeneous catalysts for converting synthesis gas to organic compounds.

10 Claims, 2 Drawing Figures

TRANSITION METAL BIMETALLIC CLUSTERS OF RUTHENIUM WITH THALLIUM, INDIUM AND GALLIUM

BACKGROUND OF THE INVENTION

This invention relates to bimetallic cluster compounds. More particularly, the bimetallic cluster compounds contain a ruthenium carbido cluster and a Group IIIa metal.

Ruthenium carbido carbonyl salt anions of the formula $[Ru_6C(CO)_{16}]^{2-}$ are described in J. Organomet. Chem., 184, C33-C35 (1980). A rhodium carbonyl carbide cluster anion having the formula $[Rh_6C(CO)_{15}]^{2-}$ is described in U.S. Pat. No. 4,115,428. Mixed metal triaconta carbonyl salt clusters which may contain ruthenium or Group Ib metals are known from U.S. Pat. Nos. 3,989,799 and 3,974,259. Other ruthenium complexes which may contain carbonyls are described in U.S. Pat. Nos. 3,793,355 and 3,786,132.

SUMMARY OF THE INVENTION

The present invention is directed to the discovery of novel bimetallic cluster compounds containing a ruthenium carbido cluster and a Group IIIa metal. The new compositions comprise a bi-metallic cluster compound of the formula $$[M]_n[(Ru_6C(CO)_{16})_2L]$$

where M is a cation, n is a number which satisfies valence requirements and L is Tl, In or Ga.

The bimetallic clusters of the invention contain two distorted $Ru_6$ octahedra with an edge from each octahedra linked to a central Group IIIa metal. The configuration about the Group IIIa metal is a slightly distorted tetrahedron with the four Ru atoms from the edges of the respective $Ru_6$ octahedra. The present compounds are homgeneous and heterogeneous catalysts or catalyst precursors for converting synthesis gas to hydrocarbons and low molecular weight oxygenates.

DETAILED DESCRIPTION OF THE INVENTION

The instant bimetallic cluster compounds of the formula $[M]_n[(RU_6C(CO)_{16})_2L]$ are derived from a ruthenium carbido cluster anion of the formula $(Ru_6C(CO)_{16})^{2-}$ and a Group IIIa metal cation, possess a Ru to Group IIIa metal ratio of 12:1, and are soluble in alcohols, ketones, ethers, alicyclic and aromatic hydrocarbons. Group IIIa is defined as set forth in the Periodic Table appearing on page 662 of "The Condensed Chemical Dictionary", 9th ed., rev. by G. G. Hawley, Van Nostrand Reinhold Company, N.Y. Preferred Group IIIa metals are Tl, In and Ga with Tl being especially preferred. Examples of preferred cluster compounds include $(C_2H_5)_4N[Ru_6C(CO)_{16})_2Tl]$
$(C_6H_5)_4As[Ru_6C(CO)_{16})_2Tl]$
$(P(C_6H_5)_3)_2N[(Ru_6C(CO)_{16})_2Tl]$ The cation M associated with the bimetallic cluster anion $[Ru_6C(CO)_{16})_2^L]^-$ is not critical and may be any cation such as alkali metal, alkaline earth metal, $N(R')_4^+$, $P(R')_4^+$, $As(R')_4^+$, $(C_6H_5)_3PNP(C_6H_5)_3^+$ and the like where R' is $C_1$-$C_{20}$ aliphatic, $C_3$-$C_8$ cycloalkyl, $C_7$-$C_{14}$ aralkyl or $C_6$-$C_{10}$ aryl. The number n satisfies the valence requirements based on the charges of the cation an bimetallic cluster anion. For monovalent cations, n is 1.

Ruthenium carbido carbonyl cluster compounds of the formula $$[M]_n[Ru_6C(CO)_{16}]^{2-}$$

are prepared by the reaction between $[MnCO_5]^-$ and $Ru_3(CO)_{12}$ in a high boiling ether. The corresponding cation m associated with the carbido carbonyl cluster anion is defined as set forth above and n is a number which satisfies the valence requirements of the cation and cluster anion.

Bimetallic cluster compounds are prepared by reacting a solution of a ruthenium carbido carbonyl cluster compound in an inert organic solvent with a $Tl^{3+}$, $In^{3+}$ or $Ga^{3+}$ salt such as $Tl(NO)_3$, $TlCl_3$, $Tl(ClO_4)_3$, $Tl(OOCCH_3)_3$, $In(NO_3)_3$ and $Ga(NO_3)_3$. Examples of suitable organic solvents include alcohols, ketones, ethers, esters and the like. A typical reaction is set forth as follows:

$$2[(C_2H_5)_4N]_2^+[Ru_6C(CO)_{16}]^{2-} + Tl(NO_3)_3 \xrightarrow{CH_3OH}$$

$$[(C_2H_5)_4N]^+[(Ru_6C(CO)_{16})_2Tl]^- + 3[(C_2H_5)_4N]^+NO_3^-$$

The reaction mixture is filtered to remove inorganic salts, stripped of solvent, dried, and the cluster compound is then recrystallized.

Figure 1:
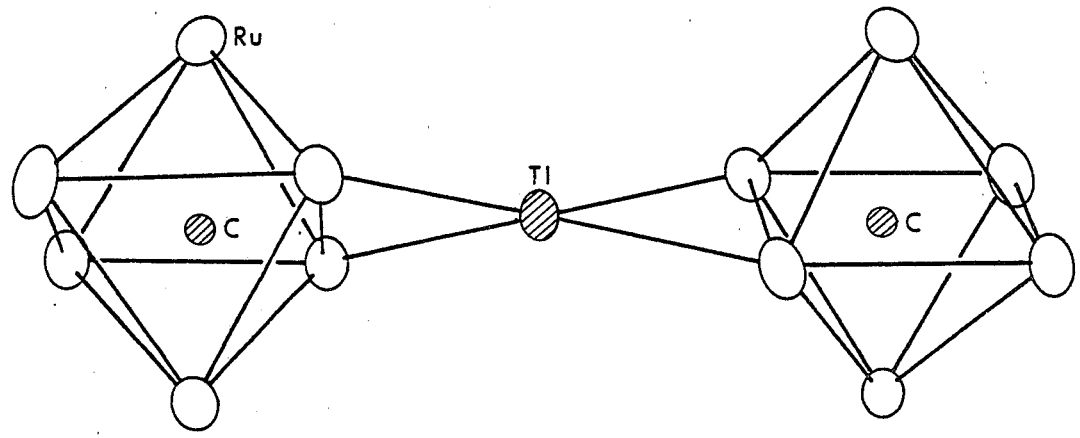
FIG. 1 is a schematic diagram showing the $(Ru_6)_2Tl$ skeleton for the compound [As $(C_6H_5)_4][(Ru_6C(CO)_{16})_2Tl]$.
Figure 2:
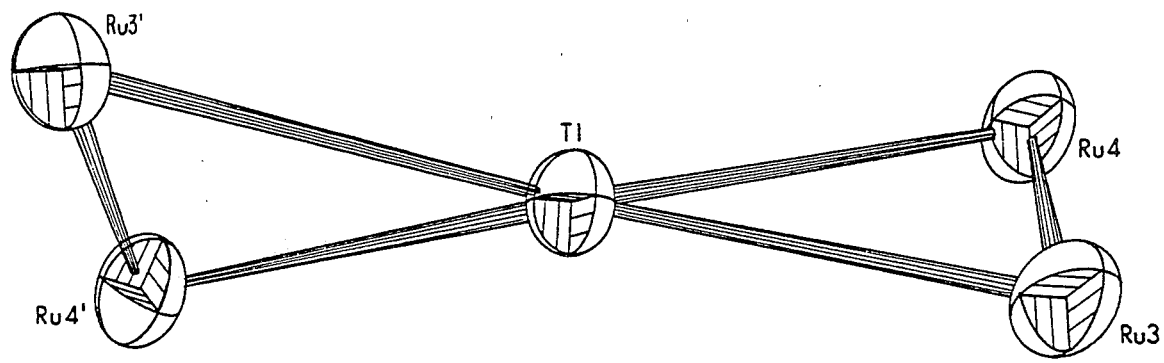
FIG. 2 is a schematic diagram showing the Ru configuration about the central Tl atom.

The structure of the bimetallic cluster compounds was determined based on a single crystal X-ray diffraction analysis of $[As(C_6H_5)_4]^+[(Ru_6C(CO)_{16})_2Tl]^-$. This compound crystallizes in space group Pl and, as shown in FIG. 1, contains a pseudo-symmetric $[(Ru_6C(CO)_{16})_2Tl]^-$ anion with two distorted $Ru_6$ octahedra, each edge being shared by two corner Ru atoms to a central Tl atom. Ru-RU distances on the shared edges adjacent to Tl are 3.103Å and 3.094Å while all other Ru-RU distances range from 2.816Å to 2.938Å. The average Ru-Tl distance is 2.822Å. Each $Ru_6$ pseudo octahedron has a central carbido-carbon atom with Ru-C distances ranging from 1.940Å to 2.185Å. The 16 CO groups associated with each $Ru_6$ pseudo-octahedron are not shown. The X-ray determination reveals that each Ru atom is associated with three CO groups; 14 CO groups are approximately linear and two are bridged. FIG. 2 illustrates in greater detail the configuration about the central Tl atom. In FIG. 2, Ru3, Ru4, RU3' and Ru4' form a slightly distorted tetrahedral configuration about the central atom.

Compositions according to the invention are useful as homogeneous and heterogeneous catalyst precursors for the preparation of alkanes and low molecular weight oxygenates from CO and $H_2$. The heterogeneous precursor may be supported on an inert support material such as refractory metal oxides or may be unsupported. These systems are interesting in that Ru metal is a known catalyst for converting synthesis gas to hydrocarbons whereas Ru compounds in solution apparently catalyze the formation of oxygenates from synthesis gas. The ruthenium in the present case is modified by thalluim, gallium or indium.

The bimetallic cluster compounds are further illustrated in the following examples.

EXAMPLE 1

A ruthenium carbido carbonyl salt of the formula $(Et_4N^+)_2[RU_6C(CO)_6]'^-$ is prepared by the reduction of $Ru_3(CO)_{12}$ with $MN(CO)_5^-$ in refluxing diglyme. 5 g of $Ru_3(CO)_{12}$ was added to a solution of 3 g $NaMn(CO)_5$ in 150 ml dry diglyme. The resulting mixture was refluxed under nitrogen for several hours. A red solution formed and the desired product could be obtained by adding $(Et_4N)^+Cl^-$. The infrared spectrum of the recystallized product shows bands at 2048(w), 2042(w), 1977(s), 1952(sh), 1918m, 1820(sh) and 1780 cm$^{-1}$. Other salts can be prepared in a similar manner.

EXAMPLE 2

A bimetallic cluster compound of the formula $[(C_2H_5)_4N][(Ru_6C(CO)_{16})_2Tl]$ is prepared by adding one equivalent of $Tl(NO_3)_3$ to a solution of $[(C_2H_5)_4N]_2[Ru_6C(CO)_{16}]$ in methanol. An immediate color change is noted and an infrared spectral analysis shows a quantitative formation of bimetallic cluster compound. After filtration of the reaction mixture, the filtrate is evaporated to dryness and extracted with methylene chloride. The $CH_2CL_2$ extractant is evaporated to dryness, and the recovered $[(C_2H_5)_4N][(Ru_6C(CO)_{16})_2Tl]$ can be further purified by recrystallization from ethanol.

EXAMPLE 3

Using the procedure of Example 2, $[As(C_6H_5)_4][Ru_6C(CO)_{16})_2Tl]$ was prepared by adding $Tl(NO_3)_3$ to a solution of $[As(C_6H_5)_4]_2[Ru_6C(CO)_{16}]$ in methanol. A pure compound was obtained by recrystallization from toluene.

EXAMPLE 4

This example demonstrates a heterogeneous $CO/H_2$ reaction using $[(C_2H_5)_4N][Ru_6C(CO)_{16})_2Tl]$ on alumina. 25 g of γ-alumina (1/16" extrudate, surface area 200 m$^2$/gm) was calcined for 15 hours at 450° C. and then cooled under $N_2$. The alumina was impregnated with a solution of 0.55 g $[(C_2H_5)_4N][(Ru_6C(CO)_{16})_2Tl]$ in tetrahydrofuran. The resulting dark red pellets were dried in vacuo at 50° C. for two hours. The so-treated alumina was charged to a Berty flow reactor and reduced at 200° C. in a stream of hydrogen (7 MPa, 100 SLH) until reduction was complete. $CO/H_2$ (40:60) was passed through the catalyst (150 SLH) which was maintained at 275° C. Effluent gases were condensed in a 0° C. trap giving two liquid phases. The aqueous phase contained predominantly linear alcohols up to $C_5$ with smaller amounts of higher alcohols. The organic phase contained linear hydrocarbons up to $C_{25}$, principally $C_7$–$C_{16}$, and linear alcohols, predominantly $C_5$–$C_9$. Total liquid yield was 27.3 g after three hours.

What is claimed is:

1. A composition of matter comprising a bimetallic cluster compound of the formula $[M]_n[(Ru_6C(CO)_{16})_2L]$ where M is alkali metal cation, alkaline earth metal cation, $N(R')_4^+$, $P(R')_4^+$ or $As(R°)_4^+$ where R' is $C_1$–$C_{20}$ aliphatic, $C_3$–$C_8$ cycloaliphatic, $C_7$–$C_{14}$ aralkyl or $C_6$–$C_{10}$ aryl, n is a number which satisfies valence requirements, and L is Tl, In or Ga.

2. The composition of claim 1 wherein L is Tl.

3. The composition of claim 1 wherein the bimetallic cluster compound is $[(C_2H_5)_4N][(Ru_6C(CO)_{16})_2Tl]$.

4. The composition of claim 1 wherein the bimetallic cluster compound is $[(C_6H_5)_4As][(Ru_6C(CO)_{16})_2Tl]$.

5. The composition of claim 1 wherein L is In or Ga.

6. A composition of matter comprising a bimetallic cluster compound of the formula $[M]_n[(Ru_6C(CO)_{16})_2Tl]$ where M is alkali metal cation, alkaline earth metal cation, $N(R')_4^{30}$ , $P(R')_4^+$ or $As(R')_4^+$ where R' is $C_1$–$C_{20}$ aliphatic, $C_3$–$C_8$ cycloaliphatic, $C_7$–$C_{14}$ aralkyl or $C_6$–$C_{10}$ aryl, and n is a number which satisfies valence requirements.

7. $[(C_2H_5)_4N][(Ru_6C(CO)_{16})_2Tl]$.

8. A catalyst precursor for $CO/H_2$ reactions comprising a bimetallic cluster compound of the formula $[M]_n[(Ru_6C(CO)_{16})_2L]$ where M is alkali metal cation, alkaline earth metal cation, $N(R')_4^+$, $P(R')_4^+$ or $As(R')_4^+$ where R' is $C_1$–$C_{20}$ aliphatic, $C_3$–$C_8$ cycloaliphatic, $C_7$–$C_{14}$ aralkyl or $C$–$C_{10}$ aryl, n is a number which satisfies valence requirements, and L is Tl, In or Ga.

9. The precursor of claim 8 wherein the bimetallic cluster is supported on an inert support material.

10. A process for preparing bimetallic cluster compounds of the formula $[M]_n[(Ru_6C(CO)_{16})_2L]$ where M is alkali metal cation, alkaline earth metal cation, $N(R')_4^+$, $P(R')_4^+$ or $As(R')_4^+$ where R' is $C_1$–$C_{20}$ aliphatic, $C_3$–$C_8$ cycloaliphatic, $C_7$–$C_{14}$ aralkyl or $C_6$–$C_{10}$ aryl, n is a number which satisfies valence requirements and L is Tl, In or Ga, which comprises reacting a solution of a ruthenium carbido cluster compound of the formula $[M]_n[Ru_6C(CO)_{16})]^{2-}$ where M and n are defined above in an inert organic solvent with a $Tl^{3+}$, $In^{3+}$ or $Ga^{3+}$ salt.

* * * * *